United States Patent
Makino et al.

(10) Patent No.: US 7,132,266 B2
(45) Date of Patent: Nov. 7, 2006

(54) METHOD AND KIT FOR ANALYZING TARGET NUCLEIC ACID FRAGMENT

(75) Inventors: Yoshihiko Makino, Saitama (JP); Yoshihiko Abe, Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/292,725

(22) Filed: Nov. 12, 2002

(65) Prior Publication Data
US 2003/0138824 A1   Jul. 24, 2003

(30) Foreign Application Priority Data
Nov. 9, 2001   (JP)   ............... 2001-345031

(51) Int. Cl.
*C12P 19/34* (2006.01)
*C12Q 1/68* (2006.01)
*C07H 21/00* (2006.01)
*C07H 21/02* (2006.01)
*C07H 21/04* (2006.01)

(52) U.S. Cl. ............... 435/91.1; 435/6; 435/91.2; 536/22.1; 536/23.1; 536/24.3; 536/24.33; 536/25.32; 536/25.6

(58) Field of Classification Search ............ 435/6, 435/91.2, 91.1; 536/22.1, 23.1, 24.3, 24.33, 536/25.3, 25.32, 25.6
See application file for complete search history.

(56) References Cited

U.S. PATENT DOCUMENTS

| | | | | |
|---|---|---|---|---|
| 6,063,572 A | * | 5/2000 | Ishiguro et al. | 435/6 |
| 6,294,670 B1 | * | 9/2001 | Takenaka | 544/225 |
| 6,316,230 B1 | * | 11/2001 | Egholm et al. | 435/6 |
| 6,361,951 B1 | * | 3/2002 | Thorp et al. | 435/6 |
| 2001/0021504 A1 | * | 9/2001 | Makino et al. | 435/6 |
| 2002/0068294 A1 | * | 6/2002 | Takenaka | 435/6 |
| 2003/0036072 A1 | * | 2/2003 | Lee et al. | 435/6 |

OTHER PUBLICATIONS

Takagi, M. (Pure Appl. Chem. (Oct. 2001), 73(10): 1573-1577).*
Stratagene Catalog (1988), p. 39.*
Takenaka et al. (Bull. Chem. Soc. Jpn. (1999) 72: 327-337).*
Stratagene catalog 1988, p. 39.*

* cited by examiner

*Primary Examiner*—Jezia Riley
(74) *Attorney, Agent, or Firm*—Reed Smith LLP

(57) ABSTRACT

A method of analyzing a target nucleic acid fragment is provided that is capable of being performed simply and promptly, by anyone, using a compact device without requirement of specific technique or complex operation. The method comprises timely detection of a double-stranded nucleic acid fragment formed during the polymerase extension reaction due to a specific base sequence of the target nucleic acid fragment as increase of an electrochemical response under the existence of an electrochemically active intercalator; and the kit utilizes the method.

12 Claims, 1 Drawing Sheet

METHOD AND KIT FOR ANALYZING TARGET NUCLEIC ACID FRAGMENT

CROSS-REFERENCES TO RELATED APPLICATIONS

This application claims priority of Japanese Application No. 2001-345031 filed Nov. 9, 2002, the complete disclosure of which is hereby incorporated by reference.

FIELD OF THE INVENTION

This invention relates to a method for analyzing a target nucleic acid fragment having a specific base sequence useful for clinical diagnosis of infection diseases caused by viruses, bacteria or the like, and for assaying genetically determined diseases caused by personal genetic characters. Particularly, this invention relates to a method for analyzing volume of a target nucleic acid fragment or a base sequence of a target nucleic acid fragment simply with high sensitivity by detecting a double-stranded nucleic acid fragment formed by a polymerase extension reaction using the target nucleic acid fragment as a template through the steps of making an electrochemically active intercalator act on the double-stranded nucleic acid fragment formed by the polymerase extension reaction and then measuring shift of an electrochemical response with electrodes; and a kit for analyzing a target nucleic acid fragment by using the method.

BACKGROUND OF THE INVENTION

Conventionally, in the clinical diagnosis of the infection disease due to viruses, bacteria or the like, identification of a pathogen such as viruses and bacteria has been carried out by culturing an analyte using body fluid such as blood, feces and sputum as a test sample. However, these methods have such problems that very long period of time is required to culture the analyte and culture itself dose not go smoothly in some cases of viruses or bacteria. Further, considering that a special technique is required to culture such analytes, they are not necessarily good methods to obtain a satisfactory result rapidly and simply.

A method, in which the disease agent such as a virus or bacterium is identified by an antibody-antigen reaction, has been also performed. It is a good method in view of rapidness and simplicity, since automatic analysis is possible. However, in an antibody detection method for detecting a disease agent as an antibody, there is a problem in sensitivity since sometimes lack of volume of the disease agent in a test sample results in impossibility of detecting the disease agent. Further, there is a problem that it is difficult to decide an antibody site specific to a kind of the disease agent. On the other hand, as for an antibody detection method for detecting an antibody produced in a body caused by infection of a disease agent, since some period of time is necessary from the infection with a disease agent to the production of the antibody, there is a problem that the disease agent can not be detected during the period of time.

On the contrary, a method for detecting a nucleic acid fragment having a specific base sequence in accordance with the kind of viruses or bacteria (a target nucleic acid fragment) by utilizing complementarity of the base sequence is the method that allows a direct identification of the disease agent. Therefore, it has come into wide use as a gene examination method such as a DNA probe method or a PCR (polymerase chain reaction) method. For example, the method for examining the HCV (hepatitis C virus) gene displays its greatest force in an inspection of the interferon (INF) administration or monitoring of cure in INF remedy fop hepatitis C, since the volume of HCV is directly known by the method.

It is further expected that genotype of respective disease agents such as viruses or bacteria will be elucidated, and that new curative medicines will be developed utilizing the genotype. In this case, it is very important not only to identify a disease agent but also to know genotype of the disease agent. The gene examination method is really the method that meets the request.

Furthermore, since the gene examination method can directly detect personal gene characteristics, in addition to identification of disease agent, it can be used to detect mutation of a gene that is the cause of hereditary disease or to detect a gene factor that affects aptitude of one's liability to life-style related to diseases such as cancer or diabetes. Especially, when the whole base sequences will be determined, it is expected that, as the post genome research, the relation between gene characteristics and disorder will be solved in greater detail, and that curative medicines using the gene characteristics will be developed. It is forecasted that demand for the gene examination method will continue to increase along with the progress of the post genome research.

However, since the gene examination methods preformed these days require a special technique, complex operation, special device and the like, only large scale examination centers can perform the gene examination method. In the examination of either infection disease caused by a virus, bacterium or the like or personal gene characteristics, an on the spot and quickest decision of guideline for diagnosis and remedy exerts greater effectiveness. In order to realize this situation, it is vital to provide a new gene examination method that can be operated by any operator with easiness and can give the examination result promptly.

For the purpose of improving simplicity and promptness, such gene examination methods have been developed that utilize detection of progress of a polymerase extension reaction using a target nucleic acid as a template. A method for detecting a generation process of an amplified product in real time as alteration of fluorescence strength during amplification of a specific nucleic acid region of a target nucleic acid fragment by PCR (Real Time PCR method) is a good method in terms of promptness since it does not require steps of electrophoresis of the amplified product after PCR and analysis of its result. Therefore this method is commercialized as the "TAQMAN" probe method (PE Biosystems Co.) or the Molecular Bean method (Stratagene Co.). However the methods utilize FRET (fluorescence resonance energy transfer), and have a problem that they require, on operation, a device that can measure alteration of fluorescence intensity and preparation of a specific hybridization probe in which a fluorescent dye and a quencher are combined to be labeled. Thus, they are no better than a special technique.

A method is described in "Igaku no Ayumi (Progress of Medical Science)" Vol. 173, No 12, 1995, in which alteration of fluorescence strength is detected while amplifying a specific nucleic acid region of a target nucleic acid under presence of fluorescent substance having a intercalator characteristics (IM-PCR: intercalation monitoring PCR method). This method has an advantage as the Real Time PCR method to the extent that it does not require a specific hybridization probe. However, the method also requires a device on operation that can measure the alteration of fluorescence strength. Further, the method has a problem in specificity since the fluorescent substance having intercalator characteristics connects to the all nucleic acid fragments existing in the system despite of presence or absence of PCR amplification of the specific nucleic acid region of the target nucleic acid fragment.

On the other hand, examples, in which amplification of DNA by PCR is detected as an electrochemical response by utilizing an intercalator, are disclosed in "2000 Electrochemistry Autumn Meeting, Preprint 2F17" and "2001 Electrochemistry Autumn Meeting, Preprint 1K11". These methods are good in terms of simplicity and a little space since they do not require measurement of fluorescence intensity alteration. However, there still remains a problem, on operation, in detection sensitivity and reproducibility of measurement, since the intercalator used is not a threading intercalator having redox activity and detection of DNA amplification by PCR is performed by detecting decrease of the electrochemical response. On this point, these methods are different from a method for analyzing a nucleic acid fragment according to the present invention, in which detection of a double-stranded nucleic acid fragment formed by polymerase chain reaction utilizing a target nucleic acid fragment as a template is performed by measuring increase of an electrochemical response under the presence of a threading intercalator having a redox activity.

SUMMARY OF THE INVENTION

An object of the present invention is to provide a method for analyzing a target nucleic acid fragment that can be performed by anybody simply and promptly with a compact device, and without a specific technique and a complex operation. Another object of the present invention is to provide a method for analyzing a target nucleic acid fragment that can realize a narrower space and an automatic operation to accomplish the above-mentioned object.

The present inventors have found that, to solve the above-mentioned problem, analysis of a target nucleic acid fragment with good simplicity and promptness can be performed by detecting timely a double-stranded nucleic acid fragment, which is formed by a polymerase extension reaction based on specific base sequence of the target nucleic acid fragment, as increase of an electrochemical response under presence of an electrochemically active intercalator to accomplish the present invention.

That is, the present invention is a method for analyzing amount or a base sequence of a target nucleic acid by detecting timely a double-stranded nucleic acid fragment, which is formed under presence of at least a kind of primer complementary to the target nucleic acid fragment whose at least a part of base sequence is known, at least a kind of deoxyribonucleoside triphosphate (dNTP) and at least a kind of polymerase, by a polymerase extension reaction starting from 3'-terminal of the primer utilizing the target nucleic acid fragment as a template, wherein the detection of a double-stranded nucleic acid fragment formed by the polymerase extension reaction is 3'-terminal of the primer, difference occurs in the reaction of a reaction portion by polymerase, also allowing the detection as the difference in the polymerase extension reaction.

Preferable embodiments according to other aspects of the invention are as follows:

(1) measurement of the alteration of the electrochemical response is performed by measuring increase in the electrochemical response;

(2) the electrochemically active intercalator is a threading intercalator having redox activity;

(3) the polymerase is selected from the group consisting of DNA polymerase I, the Klenow fragment of DNA polymerase I, Bst DNA polymerase and reverse transcriptase; and (4) the measurement of the electrochemical response is performed with cyclic voltammetry or differential pulse voltammetry.

Further, another aspect of the present invention is a kit comprising respective elements of a reagent for a polymerase extension reaction containing at least a kind of primer complementary to a part of a target nucleic acid to be detected, at least a kind of deoxyribonucleoside triphosphate (dNTP), and at least a kind of polymerase, and an electrochemically active threading intercalator.

DETAILED DESCRIPTION OF THE INVENTION

Figure 1:
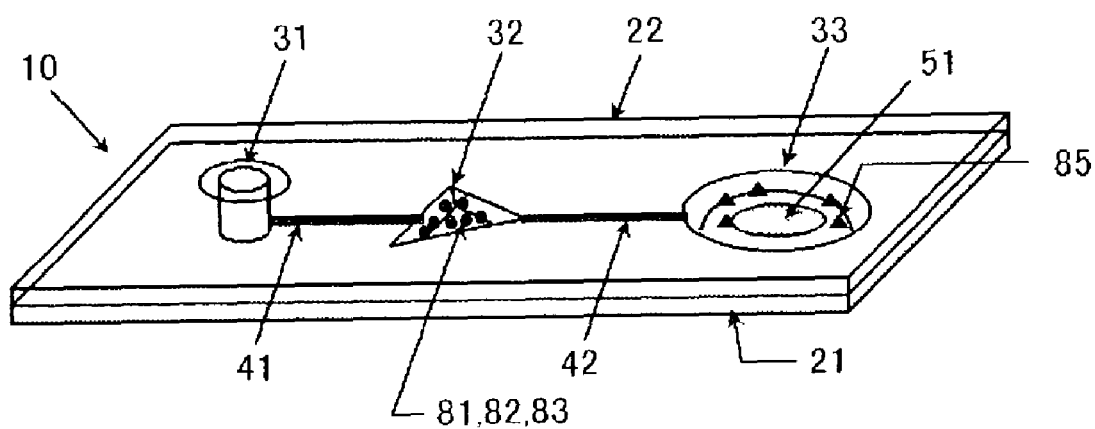
FIG. 1 is a perspective view showing an example of a kit in the shape of a cartridge according to the present invention.

Embodiments of the invention will be described in detail bellow.

(A) Target Nucleic Acid Fragment:

In the invention, a target nucleic acid fragment that is an object to be analyzed means a polynucleotide in which at least a part of base sequence is known. A genomic DNA fragment isolated from every living organism such as animals, microorganisms, bacteria and plants may be the object. An RNA fragment or a DNA fragment that can be isolated from a virus, and a cDNA fragment that is synthesized using an mRNA as a template may also be the object. It is desirable that the target nucleic acid is purified as far as possible and that additional components other than the nucleic acid fragment have been cleared away. For example, in the case where a genomic DNA fragment isolated from blood of an animal (e.g. human) is selected as the object, or a nucleic acid (DNA of RNA) fragment of an infective bacterium or a virus existing in blood is selected as the object, it is necessary to clear away adequately cell membrane of leucocyte torn down in an isolation process, hemoglobin eluted from inside of erythrocyte and other general chemical substances. Especially, the erythrocyte inhibits polymerase extension reaction that is performed subsequently.

(B) Primer Complementary to the Target Nucleic Acid:

A primer, which is complementary to the target nucleic acid, used in the present invention is an oligonucleotide having the complementary base sequence to a targeted site, in which the base sequence is known, of the target nucleic acid fragment. The primer complementary to the target nucleic acid hybridizes with the targeted site of the target nucleic acid fragment to result in progress of the polymerase extension reaction starting from 3'-terminal of the primer using the target nucleic acid fragment as the template. That is to say, the most important point in the invention is that whether or not the primer recognizes the targeted site of the target nucleic acid fragment resulting in specific hybridization. A preferable number of the base of the primer used in the invention is from 5 to 60, and the especially preferable number is from 15 to 40. When the number of the base of the primer is too small, not only the lowering of the specificity of the primer to the targeted site of the target nucleic acid is resulted in, but also the stable hybridization itself with the target nucleic acid can not be formed. On the other hand, when the number of the base of the primer is too large, the specificity also lowers since a double strand is formed between primers or in the primer due to hydrogen bond between bases.

In the case where detection of the presence of the target nucleic acid fragment is performed with the method according to the invention, corresponding to different sites of the target nucleic acid, plural primers, each of which is complementary to respective sites, may be used. By recognizing the target nucleic acid fragment at plural sites in this manner, specificity is elevated in the detection of the presence of the target nucleic acid fragment. Further, when a part of the target nucleic acid fragment is amplified (for example, with PCR method), it is also possible to design plural primers according to amplification methods. When analyzing the base sequence of the target nucleic acid fragment with the method according to the invention, especially presence of mutation or polymorphism, the primer is designed using plural kinds of bases corresponding to the mutation or polymorphism so that the part of the targeted mutation or polymorphism is included. By doing this, presence or absence of the mutation or polymorphism of the target nucleic acid fragment results in difference in the presence or absence of hybridization of the primer to the target nucleic acid fragment allowing the detection as the difference in the polymerase extension reaction. Furthermore, by setting the portion corresponding to the mutation or the polymorphism at near 3'-terminal of the primer, difference occurs in the recognition of a reaction portion by polymerase, also allowing the detection as the difference in the polymerase extension reaction.

(C) Polymerase:

When a target nucleic acid is a DNA, polymerase used in the invention is a DNA polymerase that catalyzes a complementary extension reaction, which progresses in the direction of 5'-terminal to 3'-terminal while starting from a double-stranded part formed by hybridization of a primer to a part of the target nucleic acid where has been altered to a single-strand using deoxyribonucleoside triphosphate as a raw material and the target nucleic acid as a template. Specific examples of usable DNA polymerase include DNA polymerase I, the Klenow fragment of the DNA polymerase I and Bst DNA polymerase and the like. The DNA polymerase may be selected or combined according to a purpose. For example, when a part of the target nucleic acid is amplified (for example, with PCR method), Taq DNA polymerase, which is good in heat resistance, is effectively used. When a part of the target nucleic acid is amplified by the amplification method described in "BIO INDUSTRY, Vol. 18, No. 2, 2001" (LAMP method: Loop-mediated Isothermal Amplification of DNA), Bst DNA polymerase is effectively used, which does not have a nuclease reactivity in the direction of 5'-terminal to 3'-terminal and is a chain substituting DNA polymerase that catalyzes an extension reaction while When a genomic nucleic acid or mRNA of an RNA virus is a target nucleic acid fragment, use of reverse transcriptase having reverse transcript reactivity may be possible. Further, reverse transcriptase and Taq DNA polymerase may also be used together.

(D) Polymerase Extension Reaction:

The polymerase extension reaction that may be usable in the invention includes the all complementary nucleic acid extension reactions that progresse, utilizing the target nucleic acid as a template, from 3' terminal of a primer that is complementary to the target nucleic acid as described in foregoing (B) and that has hybridized specifically to a part of a single-stranded part of the target nucleic acid as described in foregoing (A), using the polymerase described in foregoing (C) as a catalyst and using dNTP as raw material.

Hereinafter, examples are shown as to typical polymerase extension reactions and amplification reactions of the targeted portion of the target nucleic acid accompanied by the polymerase extension reaction. The simplest case is that the polymerase extension reaction in the direction of 5'-terminal to 3'-terminal is preformed just for once. This polymerase extension reaction can be performed under an isothermal condition. In this case, volume of double-stranded nucleic acid fragment generated as a result of the polymerase extension reaction is in proportion to volume of the target nucleic acid fragment existed at the beginning. That is to say, this is a good method to detect quantitatively the presence of the target nucleic acid fragment.

When volume of a target nucleic acid is small, amplification of the targeted site of the target nucleic acid is desirable with some means utilizing a polymerase extension reaction. For the amplification of the target nucleic acid, various methods that have been developed or invented up to now can be used. The PCR (polymerase chain reaction) method is the most popular and prevailed method as the method for amplifying the target nucleic acid. The PCR method is a method for amplifying the targeted site of the target nucleic acid fragment, in which following steps are periodically repeated by periodically controlling up and down of temperature of a reaction fluid; denature (a step to alter a nucleic acid fragment from a double-stranded chain to a single-stranded chain)→annealing (a step to hybridize a primer to the nucleic acid fragment altered to the single-stranded chain)→a polymerase (Taq DNA polymerase) extension reaction→denature. Finally, the targeted site of the target nucleic acid may be amplified by up to a million times of an initial volume. Therefore, a large volume of double-stranded DNA fragments, which is generated due to the polymerase extension reaction during the amplification process by the PCR method, can be accumulated resulting in an easier detection. However, when the PCR method is used, the targeted site of the target nucleic acid fragment is amplified exponentially and it is difficult in general to detect quantitatively an initial volume of the target nucleic acid fragment.

As a matter of fact, quantitative detection of an initial volume of a target nucleic acid fragment with the PCR method may be possible by determining previously relation between the initial volume of the target nucleic acid fragment and volume of double-stranded fragments produced after some number of periods (number of cycles) of amplification (that is, making previously a calibration curve), measuring timely in actual examination volume of double-stranded nucleic acid fragments produced by the PCR or in real time according to the number of periods, and utilizing the relation between the initial volume of the target nucleic acid fragments and the volume of the double-stranded nucleic acid fragments that is produced at the number of periods (number of cycles), which have been determined previously (the calibration curve).

A cycling assay method using exonuclease, which is disclosed in JP 1993-130870 A, is also one of methods for amplifying a targeted site of a target nucleic acid utilizing the polymerase extension reaction. In this method, along with a polymerase extension reaction that is carried out with a primer, which has specifically hybridized to the targeted site of the target nucleic acid, as a starting point, the primer is decomposed from the inverse direction while being acted by a 5' to 3' exonuclease. Instead of the decomposed primer, a new primer hybridizes resulting in a repeated extension reaction by the DNA polymerase. The extension reaction by the polymerase and a decomposition reaction by the exonuclease unchaining a previously extended chain are repeated periodically in turn. The polymerase extension reaction and the decomposition reaction by the exonuclease may be performed under an isothermal condition. An accumulated volume of double-stranded nucleic acid fragments generated by the repeated polymerase extension reaction is also large, resulting in an easy detection.

In these years, as an amplification method of a targeted site of a target nucleic acid fragment, a LAMP (Loop-mediated Isothermal Amplification of DNA) method is described in "BIO INDUSTRY, Vol. 18, No. 2, 2001". In this method, the targeted site of the target nucleic acid fragment is amplified as a specific structure under an isothermal condition by utilizing at least four kinds of primers that recognize complementally at least six specific sites of the target nucleic acid fragment, and a chain-substitution type Bst DNA polymerase that has no nuclease activity in the direction of 5' to 3' and catalyzes an extension reaction while liberating a double-stranded DNA on a template as a single-stranded DNA. Amplification efficiency of the LAMP method is high and a large volume of double-stranded nucleic acid fragments, which are generated by the polymerase extension reaction, is also accumulated, resulting in easy detection.

When a target nucleic acid is an RNA fragment, an extension reaction may be performed with an RNA chain as a template using a reverse transcriptase having a reverse transcript activity. Further, an RT-PCR method can be utilized, in which PCR reaction is performed subsequently to RT (reverse transcription) reaction while using the reverse transcriptase and Taq DNA polymerase together. By detecting a double-stranded DNA fragment generated by the RT or RT-PCR reaction, present volume of the RNA fragment, which is the target nucleic acid fragment, can be detected. The method is effective to detect present volume of an RNA virus.

(E) Electrochemically Active Intercalator:

An electrochemically active intercalator usable in the invention intercalates to a double-stranded nucleic acid fragment generated by the polymerase extension reaction as described in aforementioned (D) and indicates electronic response corresponding to impressed voltage. A preferable intercalator as the electrochemically active intercalator is a threading intercalator having a redox activity. As for the threading intercalator having the redox activity, it is particularly preferable to use intercalators described in JP 1997-288080 A and J. Chem. Soc. Commun., 1111, 1998.

Further, compounds shown by following general formula (1) are also preferably used as the intercalator. The intercalator shown by the formula (1) is characterized by having the peak current value when the impressed voltage ranges from 400 to 600 mV.

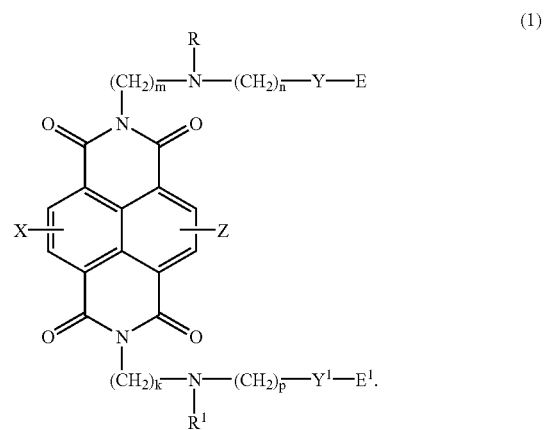

In the above formula (1), an N-substituted imino group is the group that gives solubility to the intercalator; each of R and $R^1$ represents independently from each other an atom or a group selected from the group consisting of a hydrogen atom, an alkyl group having 1 to 3 carbon atoms that may have a substituent, an acyl group having 2 to 4 carbon atoms, an aryl group having 6 to 20 carbon atoms, and an aralkyl group having 7 to 23 carbon atoms in total containing an alkyl chain having 1 to 3 carbon atoms. As the alkyl group having 1 to 3 carbon atoms, a methyl or ethyl group is preferable, and the methyl group is particularly preferable. As the acyl group having 2 to 4 carbon atoms, an acetyl group is preferable. As the aryl group having 6 to 20 carbon atoms, a phenyl or naphthyl group is preferable, and the phenyl group is particularly preferable. As the aralkyl group having 7 to 23 carbon atoms in total containing an alkyl chain having 1 to 3 carbon atoms, a benzyl group is preferable. R and $R^1$ represent preferably the same atom or group, and particularly preferably a methyl group, respectively.

As for the substituent, an atom or a group selected from a group consisting of a hydroxyl group, a halogen atom (F, Cl, Br etc.), a carboxyl group, an alkyl group having 1 to 6 carbon atoms, an alkyl amino group having 1 to 6 carbon atoms, a halogenated alkyl group having 1 to 6 carbon atoms, an aryl group having 6 to 12 carbon atoms and an alkoxy group having 1 to 6 carbon atoms can be listed. As for the number of the substituent, 1 to 12 is preferable for the alkyl group having 1 to 6 carbon atoms, the halogenated alkyl group having 1 to 6 carbon atoms or the alkoxy group having 1 to 6 carbon atoms, 1 to 3 is more preferable and 1 is particularly preferable; and 1 to 7 is preferable for the aryl group having 6 to 12 carbon atoms, 1 to 3 is more preferable and 1 is particularly preferable.

Each of Y and $Y^1$ represents independently from each other —NH—CO— group or —CO—NH— group; and —NH—CO— group is preferable. The carbonyl group or the imino group in the group combines with E and $E^1$, respectively.

Each of E and $E^1$ represents independently from each other a ferrocene having one bonding hand. The ferrocene may or may not have a substituent. When both of them have respective substituents, preferably they are the same. Specific examples of ferrocenes having a substituent are shown bellow. The substituent may be located at any site of the cyclopentadienyl group.

(X1) 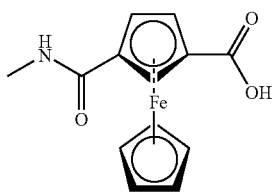

(X2) 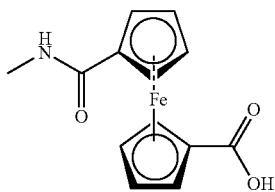

(X3) 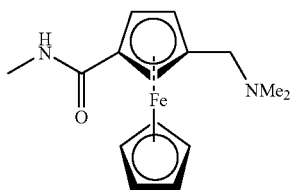

(X4) 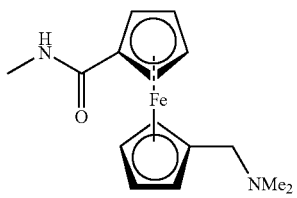

(X5) 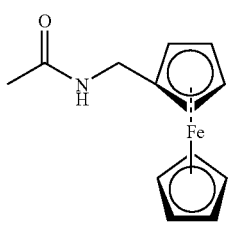

(6) 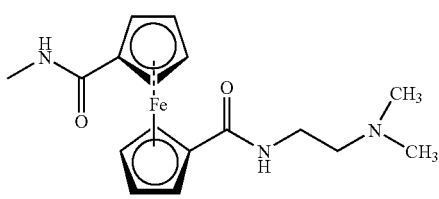

Each of X and Y represents independently from each other a hydrogen atom, a halogen atom or an alkyl group having 1 to 6 carbon atoms, and preferably the hydrogen atom. Preferable examples of the alkyl group having 1 to 6 carbon atoms are the same as those for R (or $R^1$) described above.

Each of m, n, k and p determines length of the linker moiety of the threading intercalator, and represents an integer of 1 to 6. But, respective sums of m and n, and k and p are 4 to 8. It is preferable that m and k, and n and p are the same integer, respectively, and particularly preferable that each of them is 3.

The above-described threading intercalator that is labeled with an electro-conductive group is produced simply with a high yield according to the method described in, for example, JP 1997-288080 A.

In the invention, it is particularly preferable to use the threading intercalator labeled with a group showing the redox activity that is represented by following general formula (2). The intercalator represented by the formula (2) has a characteristic of showing the peak current at an impressed voltage ranging from 100 to 400 mV.

$$E_a\text{—}L_a\text{—}X\text{—}L_b\text{—}E_b \qquad (2)$$

Here, each of $E_a$ and $E_b$ represents independently from each other a group showing the redox activity and containing a conjugated system; X represents a bivalent cyclic group; and each of $L_a$ and $L_b$ represents independently from each other a linker, which forms a linker that does not extend the respective conjugated systems of $E_a$ and $E_b$, and at least one of them is a linker having a site that gives solubility in water to the compound or having a site that may be changed to a site that gives solubility in water.

In the formula (2), it is preferable that $E_a$ and $E_b$, and $L_a$ and $L_b$ are the same group from each other, respectively. Further, it is preferable that the number of atoms composing the shortest linking path of the main chain of the linking part represented by $L_a\text{—}X\text{—}L_b$ is between 10 to 100, more preferably between 15 to 70, and particularly preferably between 20 to 50. Here, in the case where calculation of the number of atoms composing the shortest linking path of the main chain of the linking part is applied to above-mentioned ferrocene carboxylic acid N-hydroxysuccinimide ester, the number of atoms becomes 32.

Each of $E_a$ and $E_b$ is, independently from each other, preferably a redox-active group selected from the group consisting of metallocene having one or more bonding hands, 2,2'-bipyridine complex, cyclobutadiene complex, cyclopentadienyl complex, 1,10-phenanthroline complex, triphenyl phosphine complex, catecholamine, viologen, and each of them having a substituent.

The compound represented by the formula (2) above is particularly preferably a compound represented by formula (3) bellow.

$$E_a\text{—}L_{1a}\text{—}L_{2a}\text{—}X\text{—}L_{2b}\text{—}L_{1b}\text{—}E_b \qquad (3)$$

Here, each of $E_a$ and $E_b$ represents independently from each other a group having the redox activity and containing a conjugated system; each of $L_{1a}$ and $L_{1b}$ represents independently from each other a group that does not form a conjugated system to extend the conjugated systems of $E_a$ and $E_b$; each of $L_{2a}$ and $L_{2b}$ represents independently from each other a linking group having a site that gives water solubility or a linking group having a site that may be changeable to a site that gives water solubility; and X represents a bivalent cyclic group.

Each of $L_{1a}$ and $L_{1b}$ is, independently from each other, preferably a hydrocarbon group that may have a substituent, and particularly preferably an alkylene group of 1 to 6 carbon atoms that may have a substituent group or an alkenylene group of 1 to 6 carbon atoms that may have a substituent.

Each of $L_{2a}$ and $L_{2b}$ is, independently from each other, preferably a linking group containing an element other than a carbon (for example, N, O or S), and particularly preferably a linking group selected from the group consisting of an amido bonding group, an ester bonding group, an ether bonding group, a thioether bonding group, a diimido bonding group, a thiodiimido bonding group, a thioamido bonding group, an imino bonding group, a carbonyl bonding group, a thiocarbonyl bonding group, a 1,4-piperazinyl group and each of them having a substituent. The most preferable group is —NHCO— group or —CONH— group. Further, it is advantageous that $E_a$ and $E_b$, $L_{1a}$ and $L_{1b}$, and $L_{2a}$ and $L_{2b}$ are the same each other, respectively.

In the case where the threading intercalator represented by the formulae (2) or (3) is used, relatively low potential in the range of 100 to 400 mV can be utilized as the potential to be applied to electrodes during the operation of analyzing the fragment of nucleic acid.

In the formulae (2) and (3), X represents a bivalent cyclic group that may have a substituent. As for the bivalent cyclic group, planar cyclic groups are preferred. The preferable cyclic group is that selected from the group consisting of a naphthalene diimido group having a bonding hand on two nitrogen atoms, an anthracene group having a bonding hand at 2- and 6-sites or 1- and 5-sites (preferably 2- and 6-sites), an anthraquinone group having a bonding hand at the same sites as the anthracene group, a fluorene group having a bonding hand at 2- and 6-sites, a biphenylene group having a bonding hand at 2- and 6-sites, a phenanthrene group having a bonding hand at 2- and 7-sites, and a pyrene group having a bonding hand at 2- and 7-sites. The naphthalene diimido group having a bonding hand on two nitrogen atoms is particularly preferable. As for the substituent, a hydrogen atom, a halogen atom (F, Cl, Br etc.) or an alkyl group having 1 to 6 carbon atoms is preferable, and the hydrogen atom is more preferable. The preferable alkyl group having 1 to 6 carbon atoms includes a methyl group, an ethyl group and an n-propyl group.

In the formula (2), each of $L_a$ and $L_b$ is, independently from each other, a linking group that does not form a conjugated line that extends each of the conjugated line of Ea and Eb, and at least one of them is a linking group that makes the compound soluble in water or a linking group having a site capable of being converted into a site that makes the compound soluble in water. Here, "a site capable of being converted into a site that makes the compound soluble in water" means that the site is changed to be water soluble by being converted into, for example, a sulfate site when it contacts with sulfuric acid. Naturally, "a site that makes the compound soluble in water" may have a charged site such as a salt site.

It is preferable that each of La and Lb has, independently from each other, a hydrocarbon group that may have a substituent group (a group corresponding to $L_{1a}$ or $L_{1b}$ in the formula (3)) on the side adjacent to Ea or $E_b$, and that each of them has a linking group containing elements other than carbon (a group corresponding to $L_{2a}$ or $L_{2b}$ in the formula (3)) on the side adjacent to X. Accordingly, preferably each of $L_a$ and $L_b$ is the linking group corresponding to —$L_{1a}$—$L_{2a}$— or —$L_{2b}$—$L_{1b}$—, respectively, in the formula (3). Here, it is preferable that each of $L_{1a}$ and $L_{1b}$ is, independently from each other, an alkylene group having 1 to 6 carbon atoms that may have a substituent or an alkenylene group having 2 to 6 carbon atoms that may have a substituent, and that each of $L_{2a}$ and $L_{2b}$ is, independently from each other, a linking group that includes N, O or S.

As for the substituent of $L_{1a}$ and $L_{1b}$, an atom or a group selected from the group consisting of a hydroxyl group, a halogen atom, a carboxyl group, an amino group, a cyano group, a nitro group, a formyl group, a formylamino group, an alkyl group having 1 to 6 carbon atoms, an alkylamino group having 1 to 6 carbon atoms, a halogenated alkyl group having 1 to 6 carbon atoms, a cycloalkylamino group having 5 to 7 carbon atoms, a dialkylamino group having 2 to 12 carbon atoms, an aryl group having 6 to 12 carbon atoms, an aralkyl group having 7 to 18 carbon atoms in total containing an alkyl chain having 1 to 6 carbon atoms, an aralkylamino group having 7 to 18 carbon atoms in total containing an alkyl chain having 1 to 6 carbon atoms, an alkanoyl group having 2 to 7 carbon atoms, an alkanoylamino group having 2 to 7 carbon atoms, an N-alkanoyl-N-alkylamino group having 3 to 10 carbon atoms, an aminocarbonyl group, an alkoxycarbonyl group having 2 to 7 carbon atoms, a heterocyclic ring group having 2 to 10 carbon atoms containing 1 to 4 hetero atoms selected from the group consisting of S, N and O, and an aryl group having 6 to 12 carbon atoms that forms a ring and may contain an alkyl chain having 1 to 6 carbon atoms, an alkoxy chain having 1 to 6 carbon atoms or 1 to 5 halogen atoms as substituents. As for the number of the substituent, 1 to 12 are preferable for an alkylene group having 1 to 6 carbon atoms, and 1 to 3 are particularly preferable. For an alkenylene group having 1 to 6 carbon atoms, preferably the number is 1 to 10, and particularly preferably 1 to 3.

Preferably each of $L_{2a}$ and $L_{2b}$ is, independently from each other, a linking group including one or plural groups selected from the group consisting of an amido linking group, an ester linking group, an ether linking group, a thioether linking group, a diimido linking group, a thiodiimido linking group, a thioamido linking group, an imino linking group, a carbonyl linking group, a thiocarbonyl linking group, 1,4-piperazinyl group and each of them having a substituent, and particularly preferably is the amido group (—NHCO— group or —CONH— group).

The example of the substituent of $L_{2a}$ or $L_{2b}$ includes an alkyl group having 1 to 3 carbon atoms, an acyl group having 2 to 4 carbon atoms, an aryl group having 6 to 20 carbon atoms and an aralkyl group having 7 to 23 carbon atoms in total containing an alkyl chain having 1 to 3 carbon atoms. As for the alkyl group having 1 to 3 carbon atoms, a methyl or ethyl group is preferable, and the methyl group is particularly preferable. As for the acyl group having 2 to 4 carbon atoms, an acetyl group is particularly preferable. As for the aryl group having 6 to 20 carbon atoms, a phenyl or naphthyl group is preferable, and the phenyl group is particularly preferable. As for the aralkyl group having 7 to 23 carbon atoms in total containing an alkyl chain having 1 to 3 carbon atoms, a benzyl group is preferable.

In the case where both of $L_{2a}$ and $L_{2b}$ are the imino linking group, a methyl group is particularly preferable as the substituent of them. Accordingly, each of $L_{2a}$ and $L_{2b}$ is, independently from each other, more preferably a N-methyl-di(n-propylenyl)imino group or a 1,4-di(n-propylenyl)-piperazinyl group, and particularly preferably the N-methyl-di(n-propylenyl)imino group.

Each of $E_a$ and $E_b$ has redox activity and thus gives electro conductivity to the compound, and is, independently from each other, metallocene having one or more bonding hands, 2,2'-bipyridine complex, cyclobutadiene complex, cyclopentadienyl complex, 1,10-phenanthroline complex, triphenylphosphine complex, catecholamine, viologen, each of them having a substituent or the like. The ferrocene having one bonding hand that may have a substituent is particularly preferable. Preferably each of $E_a$ and $E_b$ is the same group. Specific examples of the ferrocene having a substituent are shown below. The substituent may be at any site of the cyclopentadienyl group.

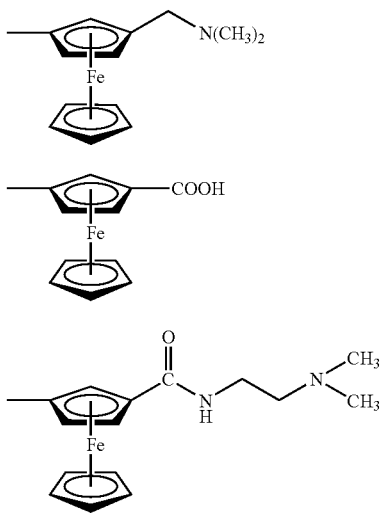

Compounds that can be advantageously utilized as the threading intercalator of the formulae (2) and (3) can be easily manufactured, for example, from a known diamine compound as a raw material by a manufacturing method in accordance with a known method (JP 1997-288080 A).

Compounds of formulae (2) and (3) can also be manufactured through the synthetic steps represented by the following formulae while starting from a known diamine compound with a low cost and high yield.

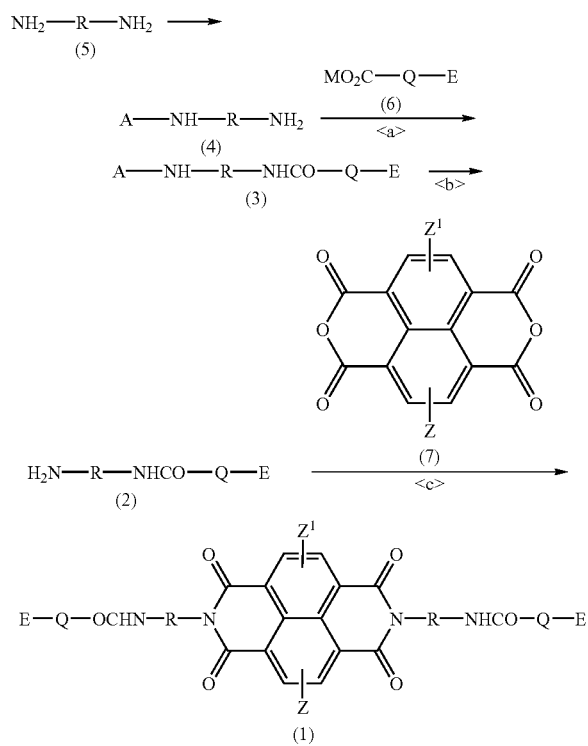

(F) Electrode:

An electrode used for measurement of an electrochemical response in the invention is, usually, provided with a terminal to output outside. Examples of material of the electrode may include, in addition to gold, carbon such as graphite and glace carbon, noble metal such as platinum, palladium and rhodium, oxide such as titanium oxide, tin oxide, manganese oxide and lead oxide, semiconductor such as Si, Ge, ZnO and CdS, and electronic conductor such as titanium. Among them, gold or glace carbon is particularly preferable. These electronic conductors may be covered with electro conductive polymer or monomolecular film. It is preferable that surface of the electrode, the glace carbon for example, has been processed by such a method as processing with potassium permanganate.

As for an electrode for use in the invention, electrodes such that wells with an electrode at the bottom thereof provided regularly in a substrate and rod-shaped substrata with an electrode at the head thereof regularly arranged, may be preferably used. Further, the electrode may be a substrate without electro conductivity on which one or more electrodes are arranged. In this case, preferably electrodes are arranged so as not to contact one another and with regularity. For example, an electrode where plural electrodes are arranged regularly on a board-like substrate may be used advantageously.

(G) Kit:

Analysis of a target nucleic acid of the invention may be performed by using a cartridge comprising an opening capable of supplying a liquid containing a fragment of the target nucleic acid whose at least a part of base sequences is known; at least one reaction sell section capable of holding at least a kind of primer complementary to a part of the target nucleic acid, at least a kind of deosyribonucleoside triphosphate (dNTP), and at least kind of polymerase; a detection section holding an electro chemically active intercalator and being provided with an electrode; and microtubes or grooves connecting the opening, the reaction cell section and the detection section each other in this order so as to be capable of moving the liquid.

In FIG. 1, an example of a kit in a shape of a cartridge according to the invention is shown. In a kit (10), a sample liquid containing the target nucleic acid is supplied through an opening (31). The opening (31) is connected with a reaction cell (32) by a microtube (41). In the reaction cell (32), at least a kind of primer (81) complementary to a part of the target nucleic acid, at least a kind of dNTP (82) and at least a kind of polymerase (83) are held previously. Further, the reaction cell (32) is connected to a detection section (33) by a microtube (42). The detection section (33) holds previously an electro chemically active threading intercalator (85), and is provided with an electrode (51). The sample liquid in which polymerase extension reaction has been progressed moves through the microtube (42) to be supplied to the detection section (33). Double-stranded nucleic acid fragments in the sample liquid supplied to the detection section (33), which have been produced by the polymerase extension reaction, are acted by the electro chemically active threading intercalators (85) and concentrated, and are detected as a shift of an electrochemical response with the electrode (51). In the kit (10), movement of the liquid between the opening (31) and the reaction cell (32), and between the reaction cell (32) and the detection section (33) may be performed by using a centrifugal force, electrophoresis, electro-osmosis or the like. The reaction cell (32), the microtubes (41, 42) and the detection section (33) are desirably sealed with a substrate body (21) and a cap (22).

Figure 2:
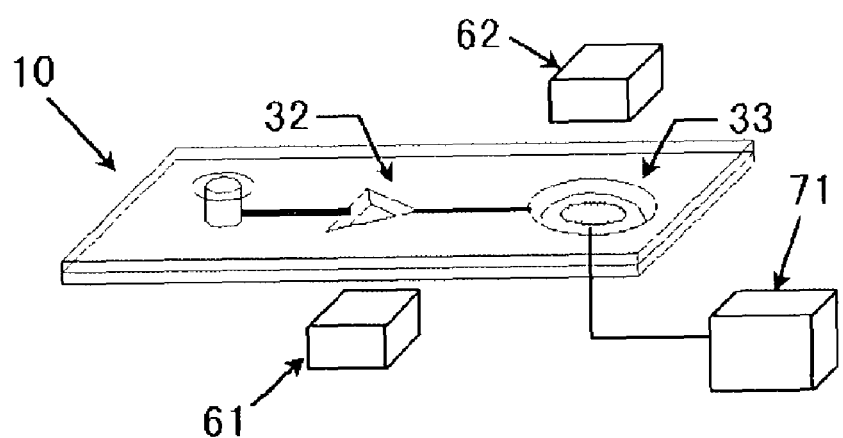
FIG. 2 is a perspective view showing the system configuration when a kit in the shape of a cartridge according to the invention is used.

When the kit (10) shown in FIG. 1 is used, it is desirable, as is shown in FIG. 2, to use a device having sections (61, 62) capable of controlling temperatures at the reaction cell (32) and the detection section (33), respectively, and a section (71) capable of detecting the shift of the electrochemical response at the same time.

Kits in the shape of cartridge that may be used in the invention are not restricted to the kit shown in FIG. 1. A cartridge may have such a shape that makes it possible to perform the polymerase extension reaction and detection of the double-stranded nucleic acid fragment produced by the polymerase extension reaction with the electrochemically active threading intercalator in the same space by providing electrodes in the reaction cell.

Further, plural sets of "an opening—a microtube—a reaction cell—a microtube—a detection section" may be provided on one cartridge by arranging them in parallel or in radial directions of concentric circles. In this case, by changing a base sequence of at least one kind of primer held in, for example, a reaction cell that is complementary to a part of a target nucleic acid fragment depending on a kind of nucleic acid that is the target, a kit, which is capable of detecting plural kinds of the target nucleic acid at the same time, may be provided.

Specific examples will be described hereinbelow for clear understanding of the invention. However, the scope of the invention is not restricted by the examples.

EXAMPLES

Example 1

Detection of a Site Relating to SRY Gene on the Short Arm of Y-chromosome (1) Preparation of a Sample Liquid of a Target Nucleic Acid Fragment Respective sample liquids of a target nucleic acid fragment were prepared by recovering respective genomic nucleic acid fragments, which were extracted and purified from blood samples collected from a male and a female respectively with a commercially available extracting and purifying kit for nucleic acid (made by QIAGEN company, QIAamp DNA Blood Mini Kit), in respective 1 ml of purified distilled waters.

(2) Preparation of a Primer

A primer was synthesized as a set of primers (primer 1 SEQ ID NO:1 and primer 2 SEQ ID NO:2) of oligonucleotide having base sequences that were designed to be capable of recognizing specifically the SRY gene on the short arm of the Y-chromosome.

<the base sequence of primers>
primer 1 SEQ ID NO:1: 5'-GATCAGCAAGCAGCTGG-GATACACGTG-3'
primer 2 SEQ ID NO:2: 5'-CTGTAGCTTCCCGTTGCG-GTG-3'

(3) Amplification of the Target Nucleic Acid Fragment by Polymerase Extension Reaction The amplification of the target nucleic acid fragment by PCR was performed using the reaction liquid having the following composition. The PCR was performed by repeating the cycle "denature, at 94° C. for 30 sec; annealing, at 65° C. for 30 sec; plylmerase extension reaction, at 72° C. for 1 min" 30 times.

<Composition of the Reaction Liquid>

| purified water | 36.5 ul |
| 10 x PCR buffer | 5 ul |
| 2.5 mM dNTP | 4 ul |
| Taq FP (Nippon Gene company) | 0.5 ul |
| 20 uM primer | 2 ul |
| 30 ng/uL target nucleic acid fragment sample liquid | 2 ul |

(4) Measurement of Shift of Electrochemical Response

Three kinds of liquid for detection having composition shown bellow were prepared by using liquids after respective reactions conducted using respective sample liquids, for the amplification reaction of the target nucleic acid fragment by polymerase extension reaction described in (3) above, containing no target nucleic acid fragment (control), containing the target nucleic acid prepared from blood collected from a male (sample M) and containing the target nucleic acid prepared from blood collected from a female (sample F).

<composition of liquid for detection>

| liquid after polymerase extension reaction | 100 ul |
| electrochemically active threading intercalator (formula (4) below) | 0.025 mg |
| 0.1 M potassium chloride - 0.1 M acetic acid buffer solution (pH 6.0) | 400 ul |

(4)

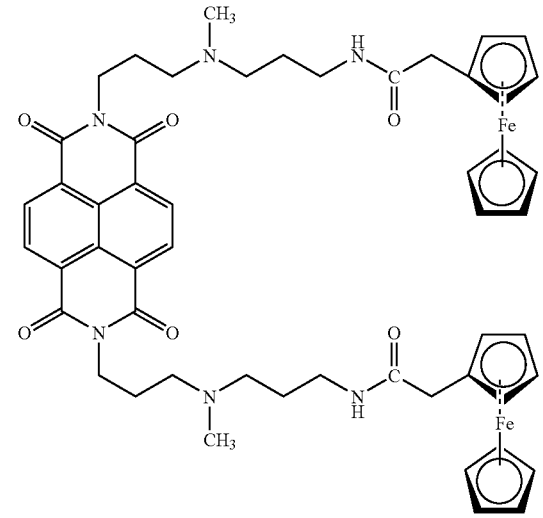

Electrodes (area of 1.0 mm²) were contacted to each of the detection liquid and differential pulse voltammetry (DPV) measurement was conducted while the impressed voltage was in the range of 100 to 700 mV. Then respective response electricity values at 260 mV of impressed voltage were found. They were −0.4 uA, −3.5 uA and −0.4 uA for the control, sample M and sample F, respectively. The DPV measurement was performed under the condition of pulse amplitude, 50 mV, pulse width, 50 mS and scanning speed, 100 mV/sec.

The result of example 1 shows that it is possible to detect specifically the site relating to SRY gene on the short arm of Y-chromosome, which exists specifically to a male. From the result, it can be seen that it is possible to detect the existence of the target nucleic acid fragment by using the method according to the invention in which increase in electrochemical response is measured after making the electrochemically active intercalator act to the double-stranded nucleic acid fragment generated according to progress of the polymerase extension reaction.

Example 2

Detection of Single Nucleotide Polymorphisms (SNPs) of a Site Relating to an Aldehyde Dehydrogenation Enzyme Gene (ALDH2 Gene)

(1) Preparation of a Sample Liquid of Target Nucleic Acid

Blood sample was collected from two persons who were known to be of ALDH2 active type and ALDH2 inactive type respectively due to difference in one specific kind of base of a site relating to ALDH2 gene, the fact having been known by previous sequencing of base sequence. Then using the blood samples, respective target nucleic acid fragment sample liquids were prepared as an ALDH2 active sample and ALDH2 inactive sample in the same manner as described in Example 1 (2).

(2) Design of a Primer

A set of primers consisting of a primer 1 (SEQ ID NO:3), and primer 2 (SEQ ID NO:4) was synthesized. The primer 1 (SEQ ID NO:3) was a primer of oligonucleotide having a base sequence designed as specific for the base sequence of the ALDH2 active type for the specific site determining the activity of ALDH2 among the sites relating to the ALDH2 gene on $12^{th}$ chromosome; and primer 2 (SEQ ID NO:4) a primer of oligonucleotide having a base sequence designed as specific for the base sequence of downstream of above-mentioned specific site.

<Base Sequence of the Primer> primer 1 SEQ ID NO:3: 5'-CAGGCATACACTGAAGT-GAAAACTG-3' (the primer becomes ALDH2 inactive type when the base sequence of GAA underlined is AAA)

primer 2 SEQ ID NO:4: 5'-AGGTCCTGAACTTCCAG-CAG-3'

(3) Measurement of Sift of Electrochemical Response

Response current value was found at impressed voltage 260 mV according to the same process as Example 1 (3) for amplification of the target nucleic acid fragment by polymerase extension reaction (PCR), and as Example 1 (4) for measurement of electrochemical response for the reaction liquid after the polymerase extension reaction. Results were –0.2 uA, –3.8 uA and –0.2 uA for respective samples of control, ALDH2 active type and ALDH2 inactive type.

The result of Example 2 shows that it is possible to detect specifically difference of the base sequence of the specific site, which determines the activity of ALDH2, among the site relating to ALDH2 gene on 12th chromosome. From the result, it can be seen that it is possible to detect the base sequence of the target nucleic acid fragment by using the method according to the invention in which increase in electrochemical response is measured after making the electrochemically active intercalator act to the double-stranded nucleic acid fragment generated according to progress of the polymerase extension reaction.

EFFECT OF THE INVENTION

The present invention provides a simple, easy and prompt method for detecting a target nucleic acid fragment having a specific base sequence, and a kit using the method. They are effective for clinical examination of infection diseases by viruses, bacterium and the like, for genetically determined diseases due to characteristics of personal heredity, and the like.

What is claimed is:

1. A kit for analyzing a target nucleic acid fragment, comprising a reagent for polymerase extension reaction including at least one primer that is free in solution and complementary to a target nucleic acid fragment to be analyzed, at least one deoxyribonucleotide triphosphate and at least one polymerase, and an electrochemically active threading intercalator which intercalates to a double-stranded nucleic acid and allows a shift of the electrochemical response.

2. A method for analyzing a target nucleic acid fragment of which at least a part of base sequence has been known, comprising:

contacting the target nucleic acid fragment with a primer that is free in solution and complementary to the target nucleic acid fragment to form into a double-stranded nucleic acid fragment;

extending the primer from a terminal by polymerase extension reaction with deoxyribonucleotide triphosphate in the presence of a polymerase utilizing the target nucleic acid fragment as a template;

contacting an electrochemically active intercalator to intercalate to the double-stranded nucleic acid fragment extended by the polymerase extension reaction where the electrochemically active intercalator is a threading intercalator having redox activity; and detecting the double-stranded nucleic acid fragment by measuring shift of electrochemical response.

3. The method for analyzing a target nucleic acid fragment according to claim 2, wherein the analysis of the target nucleic acid fragment is performed by detecting the presence or abundance of the target nucleic acid fragment or detecting mutations or polymorphisms of the target nucleic acid fragment.

4. The method for analyzing a target nucleic acid fragment according to claim 2, wherein said shift of electrochemical response is increased in the electrochemical response.

5. The method for analyzing a target nucleic acid fragment according to claim 2, wherein said polymerase is selected from the group consisting of DNA polymerase I, the Klenow fragment of DNA polymerase I, Bst DNA polymerase and reverse transcriptase.

6. The method for analyzing a target nucleic acid fragment according to claim 2, wherein said measurement of electrochemical response is cyclic voltammetry or differential pulse voltammetry.

7. The method for analyzing a target nucleic acid fragment according to claim 3, wherein said shift of electrochemical response is increased in the electrochemical response.

8. The method for analyzing a target nucleic acid fragment according to claim 3, wherein said polymerase is selected from the group consisting of DNA polymerase I, the Klenow fragment of DNA polymerase I, Bst DNA polymerase and reverse transcriptase.

9. The method for analyzing a target nucleic acid fragment according to claim 4, wherein said polymerase is selected from the group consisting of DNA polymerase I, the Klenow fragment of DNA polymerase I, Bst DNA polymerase and reverse transcriptase.

10. The method for analyzing a target nucleic acid fragment according to claim 3, wherein said measurement of electrochemical response is cyclic voltammetry or differential pulse voltammetry.

11. The method for analyzing a target nucleic acid fragment according to claim 4, wherein said measurement of electrochemical response is cyclic voltammetry or differential pulse voltammetry.

12. The method for analyzing a target nucleic acid fragment according to claim 6, wherein said measurement of electrochemical response is cyclic voltammetry or differential pulse voltammetry.

* * * * *

SEQUENCE LISTING

```
<160> NUMBER OF SEQ ID NOS: 4

<210> SEQ ID NO 1
<211> LENGTH: 27
<212> TYPE: DNA
<213> ORGANISM: Homo sapiens

<400> SEQUENCE: 1
gatcagcaag cagctgggat acacgtg                               27

<210> SEQ ID NO 2
<211> LENGTH: 21
<212> TYPE: DNA
<213> ORGANISM: Homo sapiens

<400> SEQUENCE: 2
ctgtagcttc ccgttgcggt g                                     21

<210> SEQ ID NO 3
<211> LENGTH: 25
<212> TYPE: DNA
<213> ORGANISM: Homo sapiens
```

```
<400> SEQUENCE: 3
caggcataca ctgaagtgaa aactg                                            25

<210> SEQ ID NO 4
<211> LENGTH: 20
<212> TYPE: DNA
<213> ORGANISM: Homo sapiens

<400> SEQUENCE: 4
aggtcctgaa cttccagcag                                                  20
```